United States Patent [19]

Welker et al.

[11] 4,245,650
[45] Jan. 20, 1981

[54] ELECTROMEDICAL DEVICE FOR THE ACCEPTANCE AND PROCESSING OF ELECTRIC PHYSIOLOGICAL SIGNALS

[75] Inventors: Manfred Welker; Herbert Wolf, both of Erlangen, Fed. Rep. of Germany

[73] Assignee: Siemens Aktiengesellschaft, Berlin & Munich, Fed. Rep. of Germany

[21] Appl. No.: 12,350

[22] Filed: Feb. 15, 1979

[30] Foreign Application Priority Data

Mar. 30, 1978 [DE] Fed. Rep. of Germany ....... 2813764

[51] Int. Cl.³ .............................................. A61B 5/04
[52] U.S. Cl. .................................... 128/696; 128/709; 128/908
[58] Field of Search ............... 128/696, 709, 902, 903, 128/904, 908

[56] References Cited

U.S. PATENT DOCUMENTS

| | | | |
|---|---|---|---|
| 3,690,313 | 9/1972 | Weppner et al. | 128/908 |
| 3,815,109 | 6/1974 | Carraway et al. | 128/903 |
| 3,910,257 | 10/1975 | Fletcher et al. | 128/908 |

OTHER PUBLICATIONS

Analog Devices, "Medical and Industrial Isolation Amps". no date, pp. 54–59.
Skutt et al., "IEEE Transactions on Biomedical Engineering", vol. 17, No. 4, Oct. 1970, pp. 339–348.

Primary Examiner—William E. Kamm
Attorney, Agent, or Firm—Hill, Van Santen, Steadman, Chiara & Simpson

[57] ABSTRACT

In an exemplary embodiment a multiplexer unit is arranged in the first device unit in the input channels for electric physiological signals and a demultiplexer unit is arranged in the second device unit on the side of the output channels for the time-shared scanning of the signals in the input or, respectively, output channel; and a pulse amplitude modulator and a single galvanically separating coupling location are inserted in series between the multiplexer unit of the first device unit and the demultiplexer unit of the second device unit at the interface between both device units for the de-coupled signal transmission in the time multiplex mode. By this arrangement the minimized number of coupling locations holds coupling capacitance and leakage current to a minimum with only a modest outlay for appertaining control circuitry.

5 Claims, 2 Drawing Figures

ELECTROMEDICAL DEVICE FOR THE ACCEPTANCE AND PROCESSING OF ELECTRIC PHYSIOLOGICAL SIGNALS

BACKGROUND OF THE INVENTION

The invention relates to an electromedical device for the acceptance and processing of electric physiological signals which develop in a plurality of input channels of a first device unit on the patient side and are transmitted from there with a corresponding number of output channels via galvanically separating coupling locations to a second device unit on the further processing side.

In electromedical devices of this type, i.e., where signals from a plurality of input channels of a first device unit are to be transmitted galvanically decoupled to a plurality of output channels in a second device unit, the problem exists that a corresponding galvanically separating coupling location must be provided for each of the channels. This, however, leads to an undesirably high outlay for coupling locations with the appertaining signal processing electronics.

SUMMARY OF THE INVENTION

The object of the present invention is to construct a transmission system which makes do with a minium of coupling locations and appertaining control outlay.

In a device of the type initially cited, the object is inventively achieved in that a multiplexer unit is arranged in the input channels in the first device unit and a demultiplexer unit is arranged on the side of the output channels in the second device unit for the time-shared scanning of the signals in the input or, respectively, output channels; and in that a pulse amplitude modulator and a single galvanically separating coupling location are inserted in series between the multiplexer unit of the first device unit and the demultiplexer unit of the second device unit at the interface between the two device units for the decoupled signal transmission in the time multiplex principle.

According to the invention, signal transmission in a plurality of channels now only requires a single galvanically separating coupling location. Thus, the circuit-technical outlay is limited to a minimum in construction respect. Further, a single coupling location holds the coupling capacitance between the first and the second device unit to a minimum value. The leakage current is therefore likewise limited to a minimum value.

Further advantages and details of the invention derive from the following description of an exemplary embodiment on the basis of the accompanying sheet of drawings in conjunction with the subclaims; and other objects, features and advantages will be apparent from this detailed disclosure and from the appended claims.

DETAILED DESCRIPTION

Figure 1:
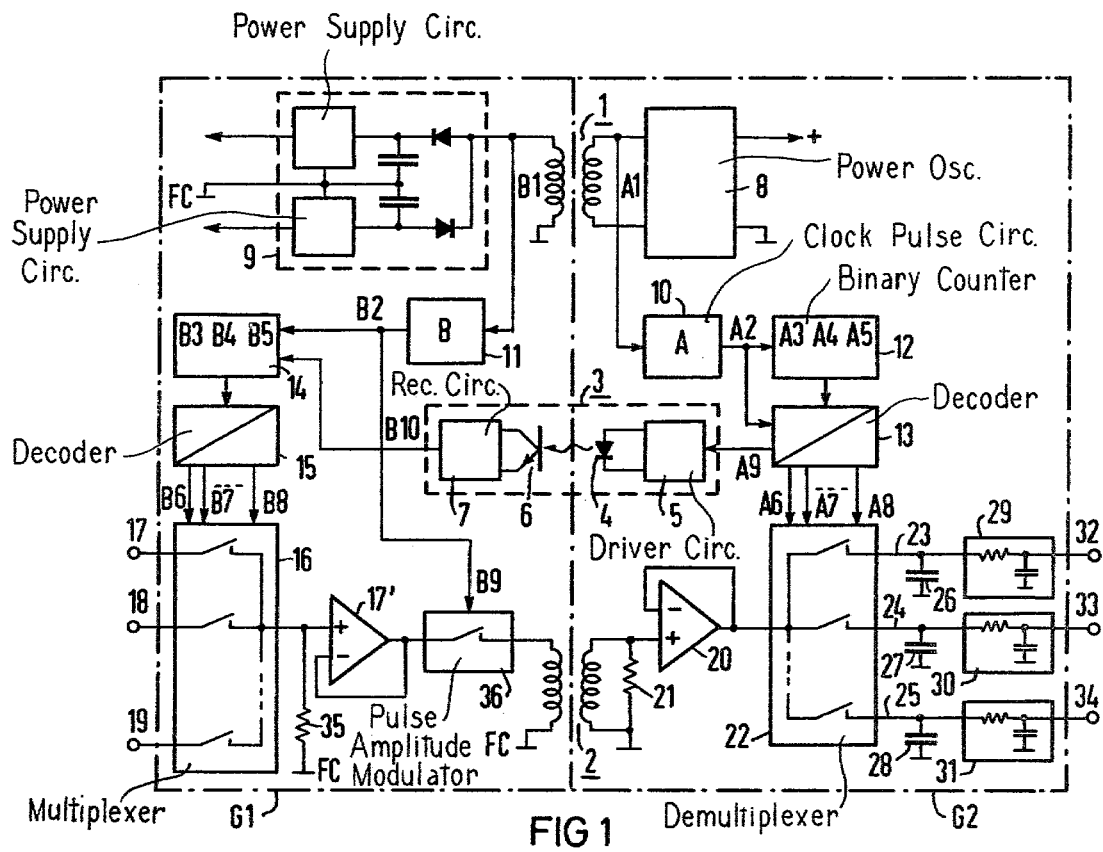
FIG. 1 shows an exemplary embodiment of the invention in basic circuit diagram.
Figure 2:
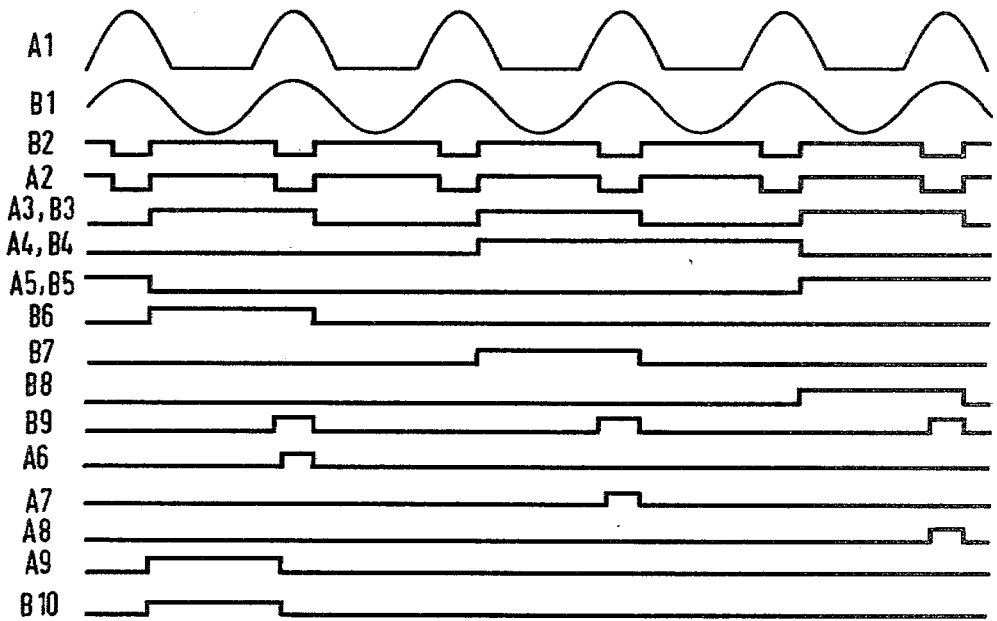
FIG. 2 shows a pulse diagram of the significant signals occurring in the basic circuit diagram of FIG. 1.

In FIG. 1, G1 designates a first device unit on the patient side and G2 designates a second device unit on the further processing side. Three galvanically separating coupling locations are located at the interface between the two device units G1 and G2. The first coupling location is an inductive power transmitter 1, the second coupling location is an inductive signal transmitter 2 and the third coupling location is an optocoupler 3.

A power oscillator 8 with an oscillator frequency of about $f \approx 50$ kHz is connected to the primary of the power transmitter 1. A power supply unit 9 lies on the secondary side of the transmitter 1. One respective signal is tapped from both sides of the transmitter 1 and is delivered to a clock pulse preparation circuit 10 or 11, respectively. In the clock pulse preparation circuit 10, a counting pulse for a post-connected binary counter 12 with a counting range of 0 through n is gained from the oscillator frequency f. By means of post-connected decoder 13, the binary counter reading of the counter 12 is respectively converted into a one out of n-code. In a corresponding manner, the counting pulse gained with the clock pulse preparation circuit 11 is delivered to a binary counter 14 and converted into a one out of n-code by means of decoder 15. The optocoupler 3 serves for the synchronization of the two counters 12 and 14 in the two device units G1 and G2. This optocoupler 3 comprises a light-emitting diode 4 which can be activated via a driver circuit 5. It further comprises a photo element 6 tuned to the light-emitting diode 4, for example, a phototransistor or a photodiode, with the appertaining reception circuit 7. The driver stage 5 of the light-emitting diode 4 is activated by the decoder 13. The signal received in the reception circuit 7 is transmitted to the binary counter 14. Thereby, this is set to the same counter reading as counter 12. It is thereby achieved that the counters 12 and 14 count exactly synchronously.

The signal transmitter 2 with the input-side time multiplexer unit 16 in the first device unit G1 serves for the actual signal transmission. The input channels (for example, three input channels are indicated but more generally n channels are contemplated) are designated with 17, 18 and 19. By means of the multiplexer unit 16, the channels 17 through 19 are scanned in temporal succession. The scanning signal is supplied to a feedback amplifier 17' and is conducted from there via a pulse amplitude modulator 36 to the signal coupling location 2. After transmission into the second device unit G2, the reception signal is delivered to an operational amplifier 20 for the purpose of impedance matching. From the output of the matching element 20, it finally reaches a demultiplexer unit 22 with storage capacitors 26, 27 and 28 at the output lines 23, 24 and 25. After filtering in the output filters 29, 30, 31, the separated output signals are yielded at the outputs 32, 33 and 34.

The control of the time multiplexer unit 16, of the demultiplexer unit 22, and of the pulse amplitude modulator 36 ensues by means of the output signals of the pulse preparation circuits 10 or 11, respectively, as a function of the frequency of the central oscillator 8. The ohmic resistance 35 pre-connected to the amplifier 17' prevents overdriving of the amplifier when no input signal is connected to the amplifier proceeding from the multiplexer 16 (open multiplexer switch). Further, the resistor 21 at the input of the impedance converter 20 defines, together with the inductance of the transmitter 2, a time constant which is smaller than the time between two scanning pulses of the pulse amplitude modulator 36. It is hereby achieved that the energy accepted during the scanning time of the modulator is entirely removed in the time between two scanning pulses. This guarantees good channel separation with an optimally low channel crosstalk. The time duration between the scanning pulses of the pulse amplitude modulator 36 preferably lies in the range equal to or greater than five ($\geq 5$) times the time constant. With its value of resistance, the resistor 21 also determines the shutdown voltage at the transmitter 2 at the shutdown time of the pulse amplitude modulator 36. The shutdown voltage should be smaller than or, respectively, equal to the maximum allowable signal voltage of the pulse amplitude modulator 36.

It will be apparent that many modifications and variations may be effected without departing from the scope of the novel concepts and teachings of the present invention.

We claim as our invention:

1. An electromedical device for the acceptance and processing of electrical physiological signals, comprising a first device unit for association with a patient, having a multiplexer unit with a plurality of input channels for receiving respective input physiological signals from the patient, having an output, and having timing and synchronization input means, said multiplexer unit comprising means for scanning said input channels and supplying a scanning signal to said output thereof in accordance with said input physiological signals, a second device unit having a demultiplexer unit with a number of output channels corresponding to the respective input channels, and haviing timing and synchronizing input means for controlling demultiplexing operation of said demultiplexer unit, said demultiplexer unit having an input and having means for supplying output physiological signals to the respective output channels in accordance with a scanning signal at said input thereof, galvanically separating coupling means for coupling with the output of said multiplexer unit of the first device unit and connected wtih said input of said demultiplexer unit of said second device unit, a pulse amplitude modulator connected in series with the output of said multiplexer unit and connected with said demultiplexer unit via said galvanically separating coupling means for supplying scanning pulses in accordance with the scanning signal from said multiplexer unit, and having a control input for receiving timing pulses controlling the supply of the scanning pulses to said galvanically separating coupling means, central oscillator means coupled with the timing and synchronizing input means of said multiplexer unit and of said demultiplexer unit and coupled with said control input of said pulse amplitude modulator for supplying timing pulses thereto for effecting the channel selection for the multiplexer unit and for the demultiplexer unit, and for controlling the supply of the scanning pulses to said input of said demultiplexer unit via said galvanically separating coupling means, and synchronizing control means coupled with the timing and synchronizing input means of said multiplexer unit and of said demultiplexer unit for synchronizing the operation thereof.

2. An electromedical device according to claim 1 with said central oscillator means comprising a single power oscillator in said second device unit and having a further galvanically separating coupling means for coupling with the first device unit to provide a voltage supply therefor.

3. An electromedical device according to claim 1 with said synchronizing control means having a further galvanically separating coupling means providing a synchronizing channel between the multiplexer unit and the demultiplexer unit and comprising an optocoupler for the transmission synchronizing pulses.

4. A device according to claim 1, characterized in that an inductive transmitter is connected with the pulse amplitude modulator and responds to the scanning pulses therefrom with a time constant smaller than the time interval between two succesive scanning pulses supplied by the pulse amplitude modulator, said inductive transmitter forming part of the galvanically separating coupling means between the pulse amplitude modulator and the demultiplexer unit.

5. A device according to claim 4, characterized in that time duration between two successive scanning pulses supplied by pulse amplitude modulator lies in the range equal to or greater than five ($\geq 5$) times the time constant of the inductive transmitter.

* * * * *